US00PP34579P2

(12) United States Plant Patent
Barnes

(10) Patent No.: US PP34,579 P2
(45) Date of Patent: Sep. 13, 2022

(54) ***BOUVARDIA* PLANT NAMED 'WINBUESLST'**

(50) Latin Name: *Bouvardia hybrida*
Varietal Denomination: 'WINBUESLST'

(71) Applicant: Brent Barnes, Riverside, CA (US)

(72) Inventor: Brent Barnes, Riverside, CA (US)

(73) Assignee: Wingen llc, Campbell, CA (US)

( * ) Notice: Subject to any disclaimer, the term of this patent is extended or adjusted under 35 U.S.C. 154(b) by 0 days.

(21) Appl. No.: 17/705,757

(22) Filed: Mar. 28, 2022

(51) Int. Cl.
*A01H 5/02* (2018.01)
*A01H 6/76* (2018.01)

(52) U.S. Cl.
USPC ..... Plt./352
CPC ..... *A01H 6/76* (2018.05)

(58) Field of Classification Search
USPC ..... Plt./352
CPC ..... A01H 6/76; A01H 5/02
See application file for complete search history.

*Primary Examiner* — Keith O. Robinson
(74) *Attorney, Agent, or Firm* — Cassandra Bright

(57) ABSTRACT

A new and distinct cultivar of *Bouvardia* plant named 'WINBUESLST' is disclosed, characterized by self-cleaning, bright red-orange flowers. Plants are globose in form, compact and dwarf. Plants have a re-blooming habit. The new variety is a *Bouvardia*, typically produced as an ornamental plant.

2 Drawing Sheets

Figure 1:
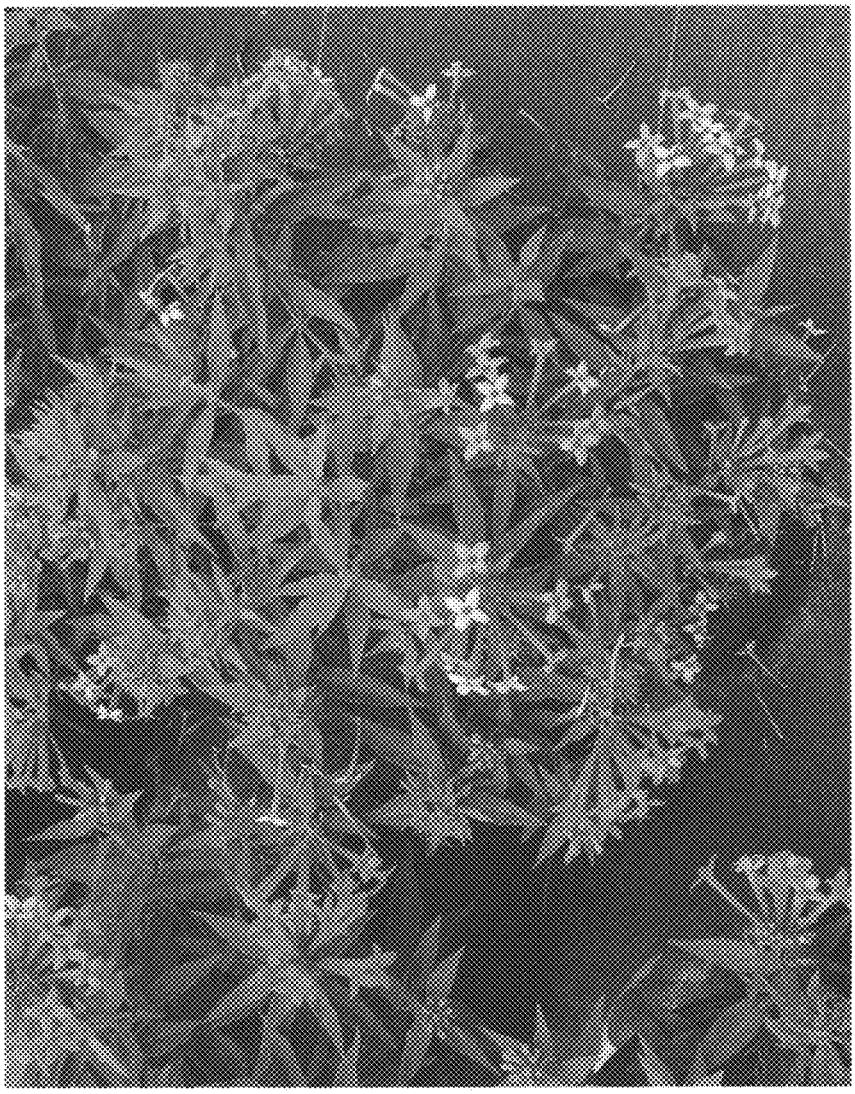

Latin name of the genus and species: *Bouvardia hybrida*.
Variety denomination: 'WINBUESLST'.

BACKGROUND OF THE INVENTION

The new *Bouvardia* cultivar is a product of a planned breeding program conducted by the inventor. The objective of the breeding program was to produce new, floriferous *Bouvardia* cultivars with dwarf plant forms, and vibrant flower colors. The cross resulting in this new variety was made in September of 2015, at a research nursery in Bonsall, Calif.

The seed parent is the unpatented, proprietary variety of *Bouvardia hybrida* referred to as '14BouB001-03'. The pollen parent is the unpatented, proprietary variety of *Bouvardia ternifolia* referred to as '*Bouvardia* Texas #17'. The new variety was identified and selected as a potentially interesting selection in the Summer of 2016. Selection was made at the same nursery in Bonsall, Calif.

Asexual reproduction of the new cultivar 'WINBUESLST' was first performed in August 2016 in Bonsall, Calif., by tip cuttings. Subsequent propagation has shown that the unique features of this cultivar are stable and reproduced true to type in successive generations.

SUMMARY OF THE INVENTION

The cultivar 'WINBUESLST' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'WINBUESLST'. These characteristics in combination distinguish 'WINBUESLST' as a new and distinct *Bouvardia* cultivar:

1. Rounded/globose plant form.
2. Bright red-orange flower color

3. Reblooming, self-cleaning flowering.
4. Compact and dwarf growth habit.

PARENT COMPARISONS

Plants of the new cultivar 'WINBUESLST' are similar to the seed parent in most horticultural characteristics. However, characteristics of the new cultivar differ in the following:

1. The new variety has orange-red flowers, while the seed parent has light pink/coral flowers.
2. Flowers of the new variety have a shorter floral tube than flowers of the seed parent.
3. The new variety produces smaller leaves than the seed parent.

Plants of the new cultivar 'WINBUESLST' are similar to the pollen parent in most horticultural characteristics. However, characteristics of the new cultivar differ in the following:

1. The new variety has a rounded/globose growth habit; the pollen parent has an upright plant habit.
2. The new variety has larger leaves than the pollen parent.

COMMERCIAL COMPARISON

Plants of 'WINBUESLST' are similar in some horticultural characteristics to the variety *Bouvardia ternifolia* 'Scarlet Hummer', unpatented. The new variety, however, differs in the following:

1. Flowers of 'WINBUESLST' have a different color throat than petals. Flowers of 'Scarlet Hummer' are a single color.
2. Flowers of 'WINBUESLST' are more orange-red; flowers of 'Scarlet Hummer' are red.

BRIEF DESCRIPTION OF THE PHOTOGRAPHS

The accompanying photograph in FIG. 1 illustrates in full color a typical plant of 'WINBUESLST' grown in a poly-greenhouse at a commercial nursery in Grand Haven, Mich. This plant is approximately 2 years old, shown in a 2 gallon pot.

Figure 2:
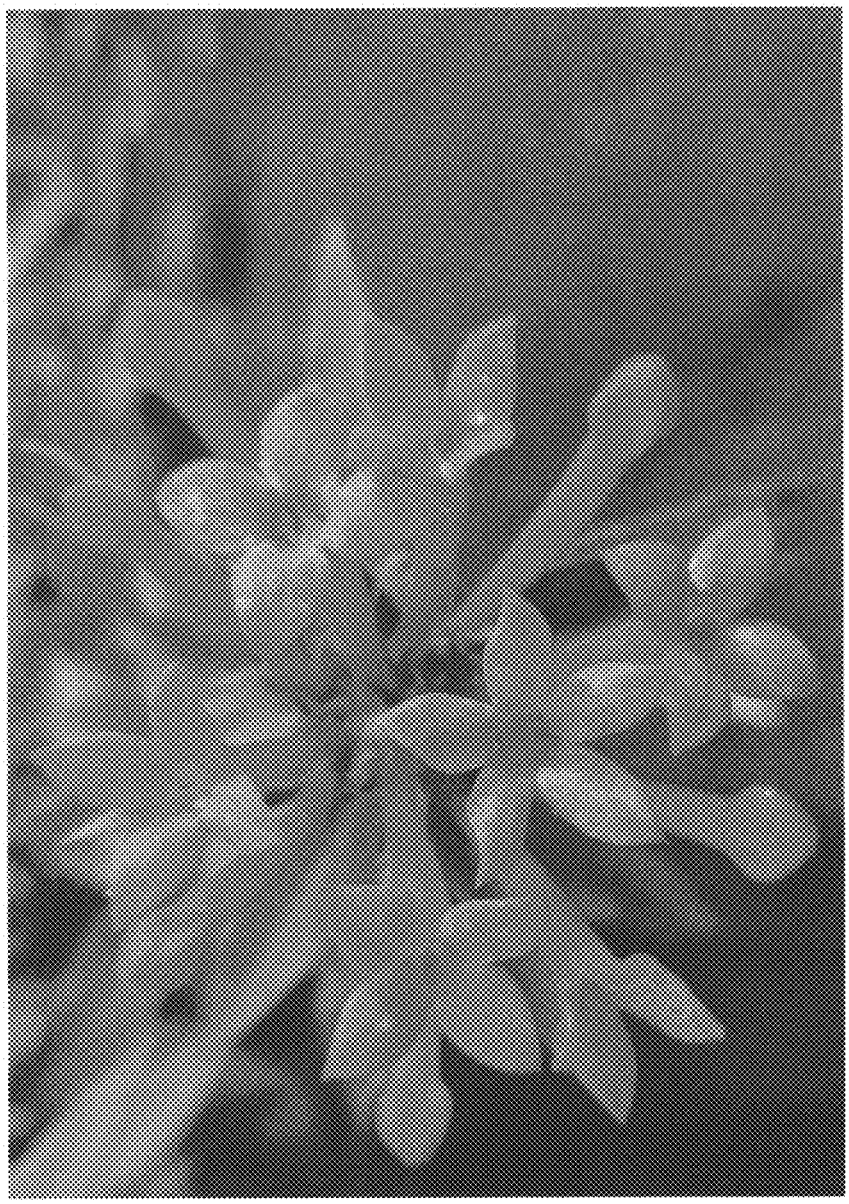

FIG. 2 illustrates a closer view of the flowers.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015, except where general terms of ordinary dictionary significance are used. The following observations and measurements describe a 'WINBUESLST' plant. This plant was grown in a poly-greenhouse in a 3 gallon container, in Grand Haven, Mich. The plant described is approximately 2-3 years old. Temperatures ranged from 5-10° C. at night and 18° C. to 27° C. during the day. No artificial light, photoperiodic treatments were given to the plants. Measurements and numerical values represent averages of typical plant types.

Botanical classification: *Bouvardia hybrida* 'WINBUESLST'.

PROPAGATION

Time to initiate roots: About 7 days at approximately 18° C. to 27° C.

Time to produce a rooted plant: About 5 weeks.

Root description: Sparse to moderate density of freely branching, thing roots. Tan in color, not effectively measured with a color chart.

PLANT

Plant type: Perennial.

Age of plant described: Approximately 2 to 3 years old.

Growth habit: Globose.

Height: 50 cm.

Plant spread: 65 cm.

Growth rate: Moderate.

Plant vigor: Good.

Branching characteristics: Basal branching, upright branching, pinching required.

Length of lateral branches: 45 cm.

Diameter of lateral branches: 4 mm.

Quantity of lateral branches: About 20.

Internode length: 4.5 cm.

Stem:

- *Aspect.*—45° to 75°.
- *Strength.*—Strong, somewhat rigid.
- *Color.*—New growth: Greyed-Purple 183C and 183D upper section. Yellow-Green 145B lower section. Old Growth: Near Greyed-Green 196A.
- *Pubescence.*—Very slight velvety pubescence on new growth only.

FOLIAGE

Leaf:

- *Arrangement.*—Whorled.
- *Shape.*—Lanceolate.
- *Average length.*—4 cm.
- *Average width.*—1.25 cm.
- *Pubescence.*—Very slight velvety pubescence on upper and lower surfaces.
- *Apex.*—Acuminate.
- *Base.*—Attenuate.
- *Margin.*—Entire.
- *Color.*—Young, Upper side: RHS Green N137B. Young, Under side: RHS Yellow-Green 147B. Mature, Upper side: RHS Green N137B. Mature, Under side: RHS Yellow-Green 147B.
- *Venation.*—Type: Pinnate. Venation Color, Upper side: RHS Yellow-Green 147B. Venation Color, Under side: RHS Yellow-Green 147B.

Petiole:

- *Leaf.*—Length: 3.5 mm. Diameter: 1.5 mm. Color: Upper Surface: RHS Green N137B. Lower Surface: RHS Yellow-Green 147B. Texture: Velvety.

FLOWER

Natural flowering season: Summer.

Inflorescence and flower type and habit: Terminal clusters of salverform flowers.

Inflorescence:

- *Diameter.*—Approximately 8 to 12 cm.
- *Height.*—Average 5.0 cm.
- *Flowers per inflorescence.*—10 to 15.

Individual flower:

- *Persistent or self-cleaning.*—Self-cleaning.
- *Fragrance.*—None.
- *Aspect.*—Upright and outwardly facing.
- *Diameter.*—1.75 cm.
- *Length/depth.*—3.0 cm.
- *Tube length.*—3.0 cm.
- *Throat diameter, proximal end.*—4 mm.
- *Throat diameter, distal end.*—2.5 mm.

Bud:

- *Shape.*—Oblong, flaring to deltate at tip.
- *Length.*—2 cm to 2.5 cm.
- *Diameter.*—3 mm.
- *Color.*—RHS Greyed-red 180B fading to Red 41B at tip.

Petals:

- *Quantity.*—4 to 5.
- *Arrangement.*—4 to 5 lobes arranged in a whorl around throat opening.
- *Length from throat.*—8 mm.
- *Width.*—5 mm.
- *Shape.*—Ovate.
- *Apex.*—Acute.
- *Base.*—Fused.
- *Margin.*—Entire.
- *Petal texture.*—Smooth and silky.
- *Color.*—When Opening, Upper Surface: RHS Red 41B. When Opening, Lower Surface: RHS Red 41B. Fully Opened, Upper Surface: RHS Red 41B. Fully Opened, Lower Surface: RHS Red 41B. Fading, Upper Surface: RHS Red 41D. Fading, Lower Surface: RHS Red 41D.
- *Tube color.*—Near RHS Greyed-Red 180B.
- *Throat color.*—Near RHS Greyed-Red 180B.

Sepals:

- *Arrangement.*—Whorl around base.
- *Quantity.*—4.
- *Length.*—4 mm.
- *Width.*—1 mm.

*Shape*.—Acicular.
*Margin*.—Entire.
*Apex*.—Acute.
*Base*.—Fused.
*Color*.—Upper Side: RHS Green N137B. Under Side: RHS Green N137B.
*Texture*.—Upper surface: Soft, velvety pubescent. Lower surface: Soft, velvety pubescent.

Peduncles:
*Length*.—4 mm.
*Diameter*.—2 mm.
*Angle*.—Upright, 45° to 90°.
*Strength*.—Strong.
*Texture*.—Soft, velvety pubescent.
*Color*.—Near RHS Yellow-Green 145B.

Pedicels: None.

REPRODUCTIVE ORGANS

Stamens:
*Number*.—4 or 5.
*Filament length*.—Fused to interior of throat.

Anthers:
*Shape*.—Linear.
*Length*.—3 mm.
*Color*.—RHS Greyed-Orange 164D.
*Pollen color*.—RHS Greyed-Orange 164D.
*Pollen amount*.—Moderate.

Pistil:
*Number*.—1.
*Length*.—2 cm.
*Style*.—Length: 2 cm. Color: RHS White N155A.
*Stigma*.—Shape: Linear. Color: RHS Greyed-Red 182A.

OTHER CHARACTERISTICS

Seeds: Not observed.

Disease/pest resistance: Neither resistance nor susceptibility to normal diseases and pests of *Bouvardia* observed.

Temperature tolerance: Low temperature tolerance to −32° C., high temperature tolerance to at least 36° C.

What is claimed is:

1. A new and distinct cultivar of *Bouvardia* plant named 'WINBUESLST' as herein illustrated and described.

* * * * *